(12) United States Patent
Kletsov et al.

(10) Patent No.: US 10,684,693 B2
(45) Date of Patent: Jun. 16, 2020

(54) METHOD FOR RECOGNIZING A GESTURE AND AN ELECTRONIC DEVICE THEREOF

(71) Applicant: Samsung Electronics Co., Ltd., Suwon-si, Gyeonggi-do (KR)

(72) Inventors: Andrey Vladimirovich Kletsov, Moscow (RU); Alexander Gennadyevich Chernokalov, Moscow region (RU); Stanislav Vladimirovich Polonsky, Moscow (RU)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 15/892,800

(22) Filed: Feb. 9, 2018

(65) Prior Publication Data

US 2018/0253151 A1 Sep. 6, 2018

(30) Foreign Application Priority Data

Mar. 2, 2017 (RU) .............................. 2017106851
Jan. 26, 2018 (KR) ........................ 10-2018-0009832

(51) Int. Cl.
  *G06F 3/01* (2006.01)
  *G06K 9/00* (2006.01)
  (Continued)

(52) U.S. Cl.
  CPC .............. *G06F 3/017* (2013.01); *A61B 5/004* (2013.01); *A61B 5/0507* (2013.01); *A61B 5/1171* (2016.02); *G01S 7/2925* (2013.01); *G01S 7/412* (2013.01); *G01S 7/417* (2013.01); *G01S 13/0209* (2013.01); *G01S 13/06* (2013.01);
  (Continued)

(58) Field of Classification Search
  CPC .......... G06F 3/017; G06F 3/015; G06F 3/014; A61B 5/004; A61B 5/1171; A61B 5/0507; G01S 7/412; G01S 13/88; G01S 13/0209; G01S 13/06; G01S 7/2925; G01S 7/417; G06K 9/00335; G06K 9/6262
  See application file for complete search history.

(56) References Cited

U.S. PATENT DOCUMENTS 5,953,541 A 9/1999 King et al.
6,965,842 B2 11/2005 Rekimoto
(Continued)

FOREIGN PATENT DOCUMENTS

CN 1531676 A 9/2004
CN 102915111 A 2/2013
(Continued)

OTHER PUBLICATIONS

International Search Report and Written Opinion regarding Application No. PCT/KR2018/001786, dated May 28, 2018, 11 pages.
(Continued)

*Primary Examiner* — Amit Chatly

(57) ABSTRACT

To recognize a gesture and control a function in an electronic device, an operating method of an electronic device includes the operations of detecting a change of a Radio Frequency (RF) signal emitted into a body using an RF sensor, determining a gesture corresponding to the RF signal based on reference data corresponding to the gesture, and executing a function of the electronic device corresponding to the determined gesture.

20 Claims, 8 Drawing Sheets

(51) Int. Cl.

| | | |
|---|---|---|
| *G01S 7/292* | (2006.01) | |
| *G01S 13/06* | (2006.01) | |
| *G01S 7/41* | (2006.01) | |
| *G06K 9/62* | (2006.01) | |
| *A61B 5/05* | (2006.01) | |
| *G01S 13/02* | (2006.01) | |
| *G01S 13/88* | (2006.01) | |
| *A61B 5/1171* | (2016.01) | |
| *A61B 5/00* | (2006.01) | |

(52) U.S. Cl.
CPC .............. *G01S 13/88* (2013.01); *G06F 3/014* (2013.01); *G06F 3/015* (2013.01); *G06K 9/00335* (2013.01); *G06K 9/6262* (2013.01)

(56) References Cited

U.S. PATENT DOCUMENTS

| | | |
|---|---|---|
| 7,170,496 B2 | 1/2007 | Middleton |
| 8,489,065 B2 | 7/2013 | Green et al. |
| 8,572,764 B2 | 11/2013 | Thellmann |
| 8,624,836 B1 | 1/2014 | Miller et al. |
| 8,660,959 B2 | 2/2014 | Callahan |
| 8,742,885 B2 | 6/2014 | Brodersen et al. |
| 8,851,372 B2 | 10/2014 | Zhou et al. |
| 8,925,006 B2 | 12/2014 | Callahan |
| 8,965,824 B2 | 2/2015 | Chun et al. |
| 8,983,539 B1 | 3/2015 | Kim et al. |
| 8,985,442 B1 | 3/2015 | Zhou et al. |
| 9,002,420 B2 | 4/2015 | Pattikonda et al. |
| 9,042,596 B2 | 5/2015 | Connor |
| 9,044,150 B2 | 6/2015 | Brumback et al. |
| 9,049,998 B2 | 6/2015 | Brumback et al. |
| 9,098,190 B2 | 8/2015 | Zhou et al. |
| 9,100,493 B1 | 8/2015 | Zhou et al. |
| 9,104,537 B1 | 8/2015 | Penilla et al. |
| 9,153,074 B2 | 10/2015 | Zhou et al. |
| 9,176,668 B2 | 11/2015 | Eleftheriou et al. |
| 9,214,043 B2 | 12/2015 | Beaurepaire |
| 9,215,274 B2 | 12/2015 | Penilla et al. |
| 9,253,264 B2 | 2/2016 | Robinson et al. |
| 9,288,270 B1 | 3/2016 | Penilla et al. |
| 9,292,097 B1 | 3/2016 | Miller et al. |
| 9,341,844 B2 | 5/2016 | Orhand et al. |
| 9,342,829 B2 | 5/2016 | Zhou et al. |
| 2004/0243342 A1 | 12/2004 | Rekimoto |
| 2006/0092177 A1 | 5/2006 | Blasko |
| 2009/0157206 A1 | 6/2009 | Weinberg et al. |
| 2010/0103106 A1 | 4/2010 | Chui |
| 2010/0220064 A1* | 9/2010 | Griffin .................. G06F 3/0418 345/173 |
| 2011/0054360 A1 | 3/2011 | Son et al. |
| 2013/0057640 A1 | 3/2013 | Callahan |
| 2013/0060914 A1 | 3/2013 | Callahan |
| 2013/0066937 A1 | 3/2013 | Callahan |
| 2013/0082824 A1 | 4/2013 | Colley |
| 2013/0132883 A1 | 5/2013 | Vayrynen |
| 2013/0144727 A1 | 6/2013 | Morot-Gaudry et al. |
| 2013/0219345 A1 | 8/2013 | Saukko |
| 2013/0237272 A1 | 9/2013 | Prasad |
| 2013/0242262 A1 | 9/2013 | Lewis |
| 2013/0261771 A1 | 10/2013 | Ten Kate |
| 2014/0045547 A1 | 2/2014 | Singamsetty et al. |
| 2014/0089399 A1 | 3/2014 | Chun et al. |
| 2014/0095420 A1 | 4/2014 | Chun et al. |
| 2014/0128032 A1 | 5/2014 | Muthukumar |
| 2014/0168060 A1 | 6/2014 | Liao et al. |
| 2014/0178029 A1 | 6/2014 | Raheman et al. |
| 2014/0349256 A1 | 11/2014 | Connor |
| 2014/0350353 A1 | 11/2014 | Connor |
| 2014/0365979 A1 | 12/2014 | Yoon et al. |
| 2015/0026708 A1 | 1/2015 | Ahmed et al. |
| 2015/0054639 A1 | 2/2015 | Rosen |
| 2015/0073907 A1 | 3/2015 | Purves et al. |
| 2015/0074797 A1 | 3/2015 | Choi et al. |
| 2015/0092520 A1 | 4/2015 | Robison et al. |
| 2015/0102208 A1 | 4/2015 | Appelboom et al. |
| 2015/0105125 A1 | 4/2015 | Min et al. |
| 2015/0109723 A1 | 4/2015 | Holtzman |
| 2015/0111558 A1 | 4/2015 | Yang |
| 2015/0120151 A1 | 4/2015 | Akay et al. |
| 2015/0121287 A1 | 4/2015 | Fermon |
| 2015/0124566 A1 | 5/2015 | Lake et al. |
| 2015/0145653 A1 | 5/2015 | Katingari et al. |
| 2015/0185764 A1 | 7/2015 | Magi |
| 2015/0205994 A1 | 7/2015 | Yoo et al. |
| 2015/0242120 A1 | 8/2015 | Rodriguez |
| 2015/0253885 A1 | 9/2015 | Kagan et al. |
| 2015/0259110 A1 | 9/2015 | Blackburn |
| 2015/0279131 A1 | 10/2015 | Nespolo |
| 2015/0286285 A1 | 10/2015 | Pantelopoulos et al. |
| 2015/0338917 A1 | 11/2015 | Steiner et al. |
| 2015/0339696 A1 | 11/2015 | Zhou et al. |
| 2015/0355805 A1 | 12/2015 | Chandler et al. |
| 2015/0370320 A1 | 12/2015 | Connor |
| 2015/0370326 A1 | 12/2015 | Chapeskie et al. |
| 2016/0004323 A1 | 1/2016 | Pantelopoulos et al. |
| 2016/0018948 A1 | 1/2016 | Parvarandeh et al. |
| 2016/0035135 A1 | 2/2016 | Park et al. |
| 2016/0041617 A1 | 2/2016 | Poupyrev |
| 2016/0058133 A1 | 3/2016 | Fournier |
| 2016/0062320 A1 | 3/2016 | Chung |
| 2016/0062321 A1 | 3/2016 | Lee et al. |
| 2016/0077587 A1 | 3/2016 | Kienzle et al. |
| 2016/0085266 A1 | 3/2016 | Lee et al. |
| 2016/0091867 A1 | 3/2016 | Mansour et al. |
| 2016/0124500 A1 | 5/2016 | Lee et al. |
| 2016/0147401 A1 | 5/2016 | Cha |
| 2016/0154489 A1 | 6/2016 | Collins et al. |
| 2016/0162873 A1 | 6/2016 | Zhou et al. |
| 2016/0287092 A1 | 10/2016 | Zhang |
| 2016/0313801 A1* | 10/2016 | Wagner .................. G06F 3/017 |
| 2016/0379475 A1 | 12/2016 | Zack et al. |
| 2019/0011989 A1* | 1/2019 | Schwesig ............ G06K 9/00201 |

FOREIGN PATENT DOCUMENTS

| | | |
|---|---|---|
| CN | 103197529 A | 7/2013 |
| CN | 103472914 A | 12/2013 |
| CN | 104199546 A | 12/2014 |
| CN | 104238344 A | 12/2014 |
| CN | 104698831 A | 6/2015 |
| CN | 104915008 A | 9/2015 |
| CN | 204695504 U | 10/2015 |
| CN | 105022471 A | 11/2015 |
| CN | 204965089 U | 1/2016 |
| EP | 1010057 B1 | 10/2002 |
| EP | 1256871 A2 | 11/2002 |
| EP | 1394665 A1 | 3/2004 |
| EP | 2813921 A1 | 12/2014 |
| EP | 2843507 A1 | 3/2015 |
| EP | 2846224 A1 | 3/2015 |
| EP | 2863276 A2 | 4/2015 |
| EP | 2876907 A1 | 5/2015 |
| EP | 2960754 A2 | 12/2015 |
| EP | 2999208 A1 | 3/2016 |
| EP | 3016081 A1 | 5/2016 |
| EP | 3023861 A1 | 5/2016 |
| JP | H07248873 A | 9/1995 |
| JP | 2002358149 A | 12/2002 |
| RU | 2584459 C2 | 5/2016 |
| RU | 2609566 C2 | 2/2017 |
| WO | 02099614 A1 | 12/2002 |
| WO | 2009095027 A1 | 7/2009 |
| WO | 2012143603 A2 | 10/2012 |
| WO | 2014046424 A1 | 3/2014 |
| WO | 2015102713 A2 | 7/2015 |
| WO | 2016053459 A1 | 4/2016 |
| WO | 2016170011 A1 | 10/2016 |

OTHER PUBLICATIONS

Communication from a foreign patent office in a counterpart foreign application, "A device and method for gesture recognition with a RF

(56) References Cited

OTHER PUBLICATIONS sensor," Russian Application No. 2017106851/08, dated Mar. 2, 2017, 10 pages.
European Patent Office, "Supplementary European Search Report," Application No. EP 18760487.1, dated Nov. 15, 2019, 12 pages.
Bainbridge, Rachel, "Wireless Hand Gesture Capture Through Wearable Passive Tag Sensing," 2011 International Conference on Body Sensor Networks, IEEE, 2011, 5 pages.

* cited by examiner

METHOD FOR RECOGNIZING A GESTURE AND AN ELECTRONIC DEVICE THEREOF

CROSS-REFERENCE TO RELATED APPLICATION AND CLAIM OF PRIORITY

The present application claims priority under 35 U.S.C. § 119(a) to Russian Patent Application No. 2017106851, filed Mar. 2, 2017, and Korean Patent Application No. 10-2018-0009832, filed Jan. 26, 2018, the entire disclosures of each of which are hereby incorporated by reference.

TECHNICAL FIELD

The present disclosure relates generally to gesture recognition. More particularly, the present disclosure relates to a device and a method for recognizing a gesture using a Radio Frequency (RF) sensor.

BACKGROUND

With the development of electronic devices, many types of the electronic devices may be controlled by gestures of a user. In order to generate a control command for the electronic device, gesture recognition is needed. Various technologies for recognizing gestures are used in the electronic devices.

Systems employing gesture control in electronic devices have been described, for example, in the following publications:

International Patent Application Publication WO 2016/053459 A1 published on Apr. 7, 2016 and titled as "TENDON BASED MOTION AND GESTURE INPUT FROM A WEARABLE DEVICE" provides a device that detects a user's motion and gesture input by piezo pressure sensor array or light sensor array. However, the sensor arrays require tight fixing on a user's wrist to provide commands to the device or to other devices.

Patent Application Publication US2015/0370326 A1 published on Dec. 24, 2015 and titled as "SYSTEMS, ARTICLES, AND METHODS FOR WEARABLE HUMAN-ELECTRONICS INTERFACE DEVICES" provides electronic bands that employ multiple microelectromechanical systems ("MEMS") microphones to detect and distinguish between different types of tapping gestures. MEMS vibration (sound) sensors must be distributed around a wrist in a wristband. However, placement of the sensors only in a wrist may limit the information available for detection.

Patent Application Publication CN105022471 A published on Nov. 4, 2015 and titled as "DEVICE AND METHOD FOR CARRYING OUT GESTURE RECOGNITION BASED ON PRESSURE SENSOR ARRAY" provides a device for carrying out gesture recognition based on a pressure sensor array which must be placed around a wrist in a wristband. However, placement of the sensors only in a wrist may limit the information available for detection.

Patent Application Publication US2016/041617 published on Feb. 11, 2016 and titled as "RADAR-BASED GESTURE RECOGNITION" describes techniques and devices for radar-based gesture recognition. These techniques and devices may recognize gestures made in three dimensions, such as in-the-air gestures. These in-the-air gestures can be made from varying distances, such as from a person sitting on a couch to control a television, a person standing in a kitchen to control an oven or refrigerator, or at several millimeters from a desktop computer's display. The techniques and devices are capable of providing a radar field that can sense gestures. However, since the radar sensor is placed on some distance from a user, the user should attend to the fact that his hands are needed to keep in the radar field. If sensor is placed on a one hand, then the other hand will be busy with gesture control.

Furthermore, there appear to be other problems and disadvantages in applying the systems and methods of the above-described publications such as:

A signal received in detecting a gesture may be unstable due to blind periods, lacking a permanent contact of a detecting device with body of user.

The user may be required to pay attention to a device's screen.

If a user wears a device on one hand, other hand may be needed to use for controlling it, so both hands are busy with a device control.

Piezo-based pressure sensors can require tightly affixing devices to a wearer.

Installation of external sensors outside the devices may be required.

Permanent skin contact to skin may be required.

Embodiments as described herein have been made to address at least one of the problems and the disadvantages described above, and to provide at least one of the advantages described below.

SUMMARY

To address the above-discussed problems, it is a primary aspect of the present disclosure to provide methods and devices for recognizing a gesture using Radio Frequency (RF) sensors.

Certain embodiments of this disclosure provide a method and an electronic device for recognizing a gesture by switching an RF frequency band according to a required resolution or a user's movement.

Certain embodiments of this disclosure provide a method and an electronic device for generating reference data for an RF signal per gesture, recognizing a gesture according to changes of the RF signal, and controlling a function of the electronic device based on the recognized gesture.

Accordingly, certain embodiments of this disclosure a method for recognizing gestures using a radio-frequency (RF) sensor, comprising steps of: successively generating sets of RF signals by at least one transmitter and successively emitting the sets of RF signals into tissues of user body part via at least one antenna; receiving the sets of RF signals reflected from and distorted by the tissues of user body part by at least one receiver via the at least one antenna; separating each received RF signal in each set of RF signals into a first RF signal and a second RF signal by the at least one receiver, wherein the first RF signal represents amplitude and the second RF signal represents phase shift; converting each of the first RF signals and the second RF signals in each set of RF signals into digital signals by at least one analog-to-digital converter (ADC) to obtain sets of digital signals, wherein each set of digital signals is obtained from corresponding set of RF signals; processing the sets of digital signals in the CPU by an artificial neural network ("ANN") using reference data sets for recognizing gestures, wherein each reference data set is associated with particular gesture and obtained by a learning of the ANN.

According to certain embodiments, learning of the ANN is performed for each gesture of plurality of gestures and may comprise steps of: generating the set of RF signals by the at least one transmitter and emitting the set of RF signals into the tissues of user body part via the at least one antenna, when the user body part performs a gesture; receiving the set of RF signals reflected from and distorted by the tissues of user body part by the at least one receiver via the at least one antenna; separating each received RF signal into the first RF signal and the second RF signal by the at least one receiver, wherein the first RF signal represents amplitude and the second RF signal represents phase shift; converting each of the first RF signals and the second RF signals into the digital signals by the at least one ADC to obtain sets of digital signals; processing the sets of digital signals by ANN to obtain the reference data set associated with the gesture, storing the reference data set in a memory comprised in the CPU.

The step of generating the sets of RF signals may, in some embodiments of this disclosure, comprise generating the RF signals having different frequencies in the set.

The step of generating the sets of RF signals may, in certain non-limiting examples provided herein, comprise generating the sets of RF signals within low frequency band and high frequency band.

According to certain embodiments of this disclosure, the low frequency band occupies frequencies of about 1-3 GHz, and the high frequency band occupies frequencies of about 3-10 GHz.

The method according to certain embodiments may further comprise steps of: when the digital signals are obtained from the sets of RF signals generated within the low frequency band, the CPU processes the sets of digital signals by using the ANN and reference data sets for recognizing a gesture, and the ANN outputs non-zero value before the gesture is completely recognized, determining that the user body part performs the gesture; and switching the at least one transmitter to generate the RF signals within the high frequency band.

The method according to certain embodiments may further comprise steps of: measuring, by a movement detector, a vibration level of said user body part; comparing, by the CPU using the ANN, the vibration level with a threshold value, wherein the threshold value is obtained by the learning of the ANN; if the vibration level exceeds the threshold value: when the sets of RF signals are generated within the high frequency band, switching the at least one transmitter to generate the RF signals within the low frequency band, or when the sets of RF signals are generated within the low frequency band and it is determined that the user body part performs a gesture, continuing generation of the RF signals within the low frequency band.

The learning of the ANN may according to certain embodiments, further comprise steps of: measuring, by the movement detector, vibration levels of said user body part, when the said user body part performs the gestures; select a maximum vibration level among measured vibration levels; assigning the maximum vibration level as the threshold value; and storing the threshold value in a memory comprised in the CPU.

The method according to certain embodiments, may further comprise steps of: if one antenna is used for pair of the transmitter and the receiver: switching the antenna to the transmitter, when the RF signal is emitted; and switching the antenna to the receiver, when the RF signal reflected from and distorted by the tissues of user body part is received.

Accordingly, certain embodiments of this disclosure provide a device for recognizing gestures using a radio-frequency (RF) sensor, comprising: at least one antenna; at least one transmitter configured to successively generate sets of RF signals and emit the sets of RF signals into tissues of user body part via at least one antenna; at least one receiver configured to receive the sets of RF signals reflected from and distorted by the tissues of user body part via the at least one antenna, and to separate each received RF signal in each set of RF signals into a first RF signal and a second RF signal, wherein the first RF signal represents amplitude and the second RF signal represents phase shift; at least one analog-to-digital converter (ADC) configured to convert each of the first RF signals and the second RF signals in each set of RF signals into digital signals to obtain sets of digital signals, wherein each set of digital signals is obtained from corresponding set of RF signals; a central processing unit (CPU) comprising a memory, the CPU being configured to process the sets of digital signals by using the ANN and reference data sets for recognizing gestures, wherein each reference data set is associated with particular gesture and obtained by a learning of the ANN The device may according to certain embodiments be further configured to perform the learning of the ANN for each gesture of plurality of gestures, wherein: the at least one transmitter generates the set of RF signals and emits the set of RF signals into the tissues of user body part via the at least one antenna, when the user body part performs a gesture; the at least one receiver receives the set of RF signals reflected from and distorted by the tissues of user body part via the at least one antenna and separates each received RF signal into the first RF signal and the second RF signal, wherein the first RF signal represents amplitude and the second RF signal represents phase shift; the at least one ADC converts each of the first RF signals and the second RF signals into the digital signals to obtain sets of digital signals; the CPU is configured to: process the sets of digital signals by ANN to obtain the reference data set associated with the gesture; store the reference data set in the memory.

The at least one transmitter according to certain embodiments may be configured to generate the RF signals having different frequencies in the set.

The at least one transmitter may according to certain embodiments, be configured to generate the sets of RF signals within low frequency band and high frequency band.

According to certain non-limiting examples provided herein, a low frequency band occupies frequencies of about 1-3 GHz, and a high frequency band occupies frequencies of about 3-10 GHz.

When the digital signals are obtained from the sets of RF signals generated within the low frequency band, the CPU according to certain embodiments processes the sets of digital signals by using the ANN and reference data sets for recognizing a gesture, and the ANN outputs non-zero value before the gesture is completely recognized, the CPU is configured to determine that the user body part performs the gesture, and switch the at least one transmitter to generate the RF signals within the high frequency band.

The device according to certain embodiments may further comprise a movement detector configured to measure a vibration level of said user body part, wherein the CPU may be configured to: by using the ANN, compare the vibration level with a threshold value stored in the memory, wherein the threshold value is obtained by the learning of the ANN; if the vibration level exceeds the threshold value: when the at least one transmitter generates the sets of RF signals within the high frequency band, switch the at least one transmitter to generate the RF signals within the low frequency band, or when the at least one transmitter generates the sets of RF signals within the low frequency band and the CPU determines that the user body part performs a gesture, continue generation of the RF signals within the low frequency band.

According to certain embodiments of this disclosure, as part of the ANN's learning process, the movement detector measures vibration levels of said user body part, when the said user body part performs the gestures; the CPU selects a maximum vibration level among measured vibration levels, assigns the maximum vibration level as the threshold value, and stores the threshold value in the memory.

The device may, according to certain embodiments further comprise, if one antenna is used for pair of the transmitter and the receiver, a switch configured to: switch the antenna to the transmitter, when the RF signal is emitted, and switch the antenna to the receiver, when the RF signal reflected from and distorted by the tissues of user body part is received, wherein the CPU is configured to control the switch.

In the non-limiting examples described herein, movement detector is at least one of an accelerometer, a magnetic sensor, a barometer, a 3D positioner.

The device for recognizing gestures using a radio-frequency (RF) sensor may in some embodiments, be embedded into a wearable device.

The CPU may be a CPU of the wearable device into which the device for recognizing gestures using a radio-frequency (RF) sensor is embedded.

The movement detector may be a movement detector of the wearable device into which the device for recognizing gestures using a radio-frequency (RF) sensor is embedded.

The wearable device into which the said device is embedded is, in certain embodiments, at least one of smartwatch, headphone.

The device for recognizing gestures using a radio-frequency (RF) sensor may further comprise a reflector arranged on a side of user body part opposite to a side of the user body part into which the RF signals is emitted, and configured to reflect the RF signals emitted into the tissues of user body part.

According to certain embodiments of the present disclosure, a method for operating an electronic device includes detecting a change of a Radio Frequency (RF) signal emitted into a user body using an RF sensor, determining a gesture corresponding to the RF signal based on reference data per gesture, and executing a function of the electronic device corresponding to the determined gesture.

According to some embodiments of the present disclosure, an electronic device includes an RF sensor and at least one processor functionally coupled with the RF sensor. The at least one processor detects a change of RF signals emitted into a user body using the RF sensor, determines a gesture corresponding to the RF signals based on reference data per gesture, and executes a function of the electronic device corresponding to the determined gesture.

Other aspects, advantages, and salient features of the present disclosure will become apparent to those skilled in the art from the following detailed description, which, taken in conjunction with the annexed drawings, discloses exemplary embodiments of this disclosure.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

The above and other aspects, features, and advantages of certain exemplary embodiments of the present disclosure will be more apparent from the following description taken in conjunction with the accompanying drawings, in which.

Throughout the drawings, like reference numerals will be understood to refer to like parts, components and structures.

DETAILED DESCRIPTION

Figure 1:
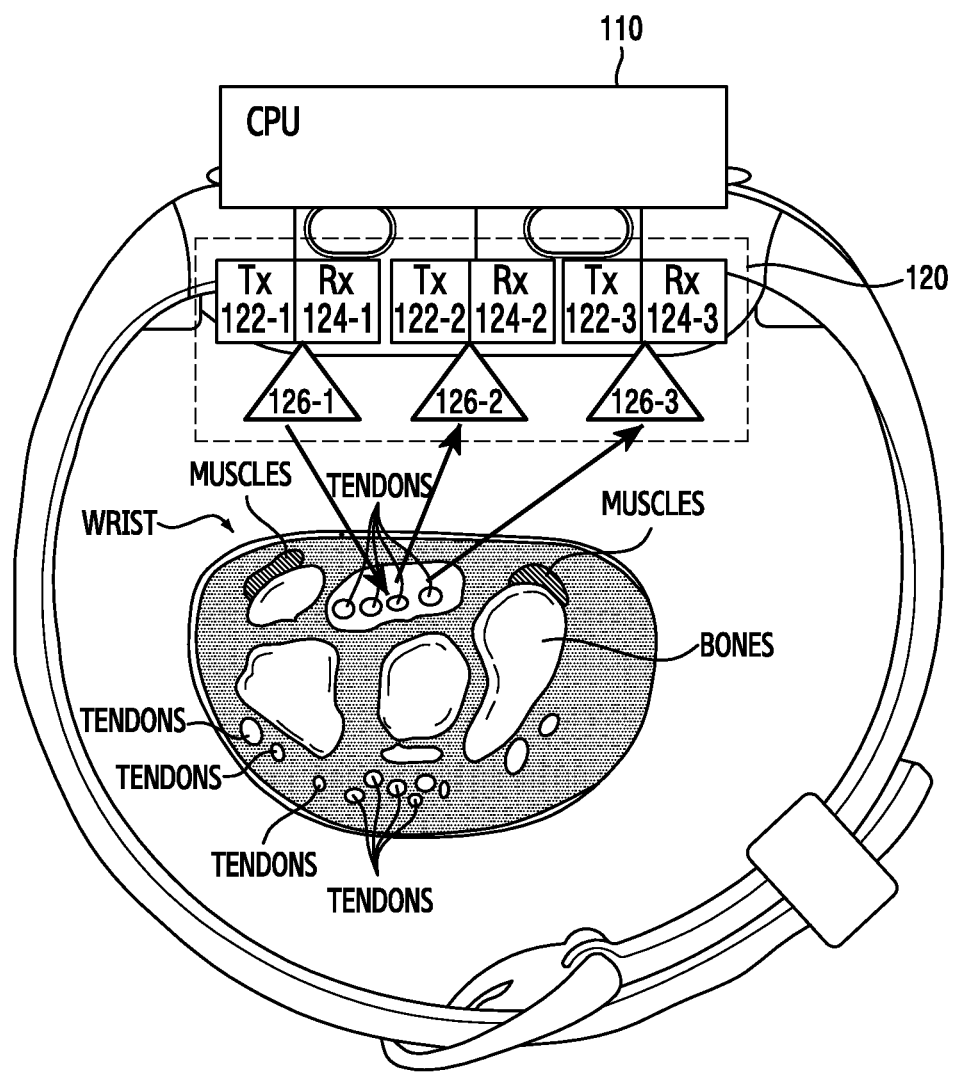
FIG. 1 illustrates an apparatus and operating context according to various embodiments of the present disclosure.

FIGS. 1 through 8, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only.

It is to be understood that the singular forms "a," "an," and "the" include plural referents unless the context clearly dictates otherwise.

It will be further understood that the terms "comprises," "comprising," "includes," and/or "including," when used herein, specify the presence of stated features, integers, operations, elements, and/or components, but do not preclude the presence or addition of one or more other features, integers, operations, elements, components, and/or groups thereof.

The terms used herein are merely for the purpose of describing particular embodiments and are not intended to limit the scope of other embodiments. As used herein, singular forms may include plural forms as well unless the context clearly indicates otherwise. Unless defined otherwise, all terms used herein, including technical and scientific terms, have the same meaning as those commonly understood by a person skilled in the art to which the present disclosure pertains. Such terms as those defined in a generally used dictionary may be interpreted to have the meanings equal to the contextual meanings in the relevant field of art, and are not to be interpreted to have ideal or excessively formal meanings unless clearly defined in the present disclosure. In some cases, even the term defined in the present disclosure should not be interpreted to exclude embodiments of the present disclosure.

In various embodiments of the present disclosure to be described below, a hardware approach will be described as an example. However, since the various embodiments of the present disclosure include a technology using both hardware and software, the present disclosure does not exclude a software-based approach.

Hereinafter, various embodiments of the present disclosure are explained in detail by referring to the attached drawings. The present disclosure relates to a method and an electronic device for recognizing a user gesture in the electronic device. Specifically, the present disclosure provides a technique for recognizing a gesture using a Radio Frequency (RF) sensor and controlling a function of the electronic device based on the recognized gesture in order to improve user convenience in the electronic device.

In the following, terms indicating control information and terms indicating components (e.g., the RF sensor) of the device are mentioned for the sake of explanations. Accordingly, the present disclosure is not limited to the terms to be described, and can use other terms having technically identical meaning.

Also, various embodiments of the present disclosure can be easily modified and applied to any electronic device of various types including an RF sensor.

Certain embodiments of the systems and methods disclosed herein recognize gestures to use in generating control commands based on recognized gesture for controlling various devices. Embodiments can be implemented as a separate wearable device to recognize gestures as described in the present disclosure and send control commands via wireless communication to other device. The wireless communication can be realized in any standards, for example, Bluetooth, Wi-Fi, GSM, ZigBee, ISM, etc. Furthermore, some embodiments can be embedded into various wearable devices to control both wearable devices. The wearable devices may be smartwatches, headphones, and other wearable devices which are to be controlled and/or control the devices coupled with the wearable devices.

FIG. 1 illustrates an apparatus and operating context according to various embodiments of the present disclosure. FIG. 1 illustrates an apparatus and operating context through the example of smartwatch. A term such as 'part' or '~er' indicates a unit for processing at least one function or operation, and can be implemented using hardware, software, or a combination of hardware and software.

An electronic device according to various embodiments of the present disclosure can include, for example, a wearable device. The wearable device can include at least one of an accessory type (e.g., a watch, a ring, a bracelet, an ankle bracelet, a necklace, glasses, a contact lens, or a Head-Mounted-Device (HMD)), a fabric or clothing embedded type (e.g., electronic garments), a body attachable type (e.g., a skin pad or a tattoo), and an implantable circuit.

Referring to the non-limiting example of FIG. 1, a device for recognizing a gesture, according to certain embodiments, can be embedded into a smartwatch. The gesture recognizing device includes a Central Processing Unit (CPU) 110, and an RF sensor 120 which includes a plurality of transmitters 122-1, 122-2, and 122-3, a plurality of receivers 124-1, 124-2, and 124-3 including Analog-to-Digital Converters (ADCs) and a plurality of antennas 126-1, 126-2, and 126-3.

In some embodiments, a transmitter (Tx) 122-1 generates RF signals and emits the generated RF signals into a user's body party on which the gesture recognizing device is positioned via the antenna 126-1. In FIG. 1, the user's body part for the smartwatch application is a wrist. In other applications, the user's body part including the gesture recognizing device can include any user body part having muscles, tendons and etc., for example, a hand, a leg, and a neck. The RF signals reflect from user body tissues and are received at the receivers (Rx) 124-2 and 124-3 via the antennas 126-2 and 126-3. The received RF signals are converted by the ADCs (not shown) into digital signals and fed to the CPU 110. The CPU 110 processes the digital signals to recognize a gesture and generates a control command based on a gesture recognition result.

According to certain embodiments of the present disclosure, the gesture recognizing device can optionally include a movement (vibration) detector (not shown in FIG. 1). The movement detector can be one of an accelerometer, a magnetic sensor, a barometer, a three-dimensional (3D) positioner of the gesture recognizing device, which determines a position of the gesture recognizing device in relation to a predetermined point in space (e.g. a user head). For example, when the wearable device such as the smartwatch includes a CPU and/or a movement detector, the CPU and/or the movement detector of the wearable device can be used as parts of the gesture recognizing device.

Figure 2:
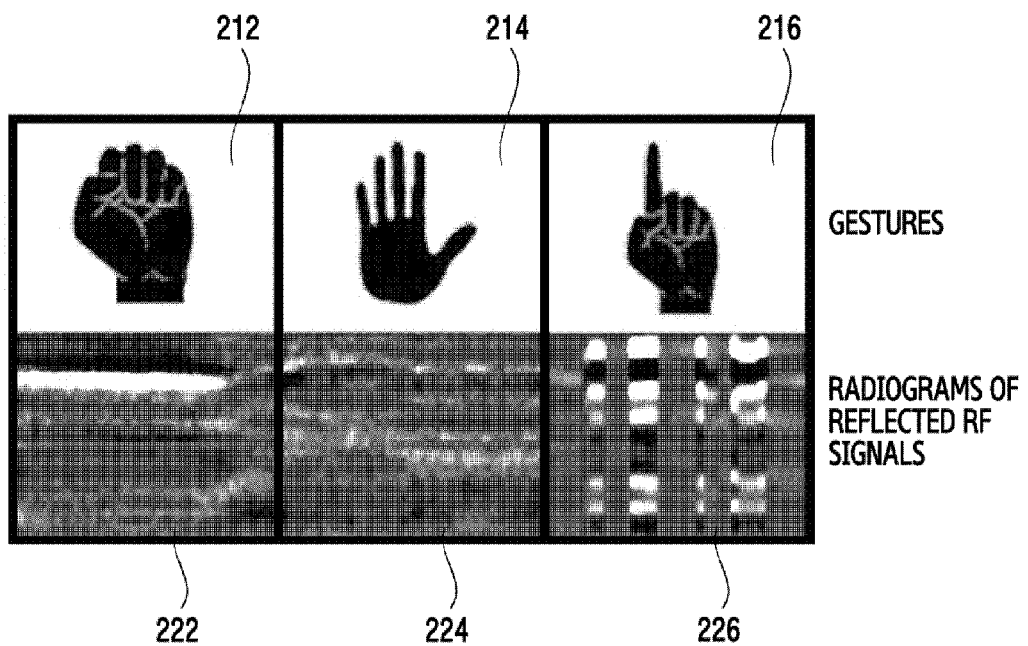
FIG. 2 illustrates Radio Frequency (RF) signals corresponding to different gestures according to various embodiments of the present disclosure.

FIG. 2 illustrates RF signals corresponding to different gestures according to various embodiments of the present disclosure. In the non-limiting example of FIG. 2, different reflected RF signals correspond to different gestures.

Referring to the non-limiting example of FIG. 2, the different gestures 212, 214, and 216 conducted by a user's body part result in different movements of user body tissues in the user's body part. The different reflected RF signals 222, 224, and 226 are caused by the different movements of the user body tissues according to the particular movements of the user body tissues. As a result of the different movements of the user body tissues in the different gestures, the reflected RF signals 222, 224, and 226 have different distortions such as attenuations (changes of amplitude) and phase shifts in relation to phases of the RF signals emitted by the transmitters and phases of the RF signals received at the receivers. Such distortions of reflected RF signals 222, 224, and 226 are recognized by an Artificial Neural Network (ANN) of the CPU as particular gestures depending on the different movements of the user body tissues to generate control commands according to the recognized gestures. Basically, the user body tissues to be monitored are tendons, but the present method can also work with muscles and so on.

Embodiments of the present disclosure may be applied in auxiliary car functions control (open boot, lock/unlock, etc.), smart home control, smart illumination control, identification (by means of gesture sequence), finger/palm gesture control, musician playing tempo, keyboard pressure rate, using neck movement, palm positioning in 3D, gesture recognition. Furthermore, embodiments according to the instant disclosure may present the following advantages: For example, when the device is placed on a back side of a palm, a user can hold real objects in hands. Accordingly, users of certain embodiments of this disclosure may able to control with "dirty" hands (while cooking, etc.) Additionally, embodiments according to this disclosure may obviate the need for complex calculations, and powerful computers may not be needed.

Hereinafter, embodiments of the present disclosure for the gesture recognizing device using the RF sensor can be provided with reference to the non-limiting examples of FIG. 3 and FIG. 4.

Figure 3:
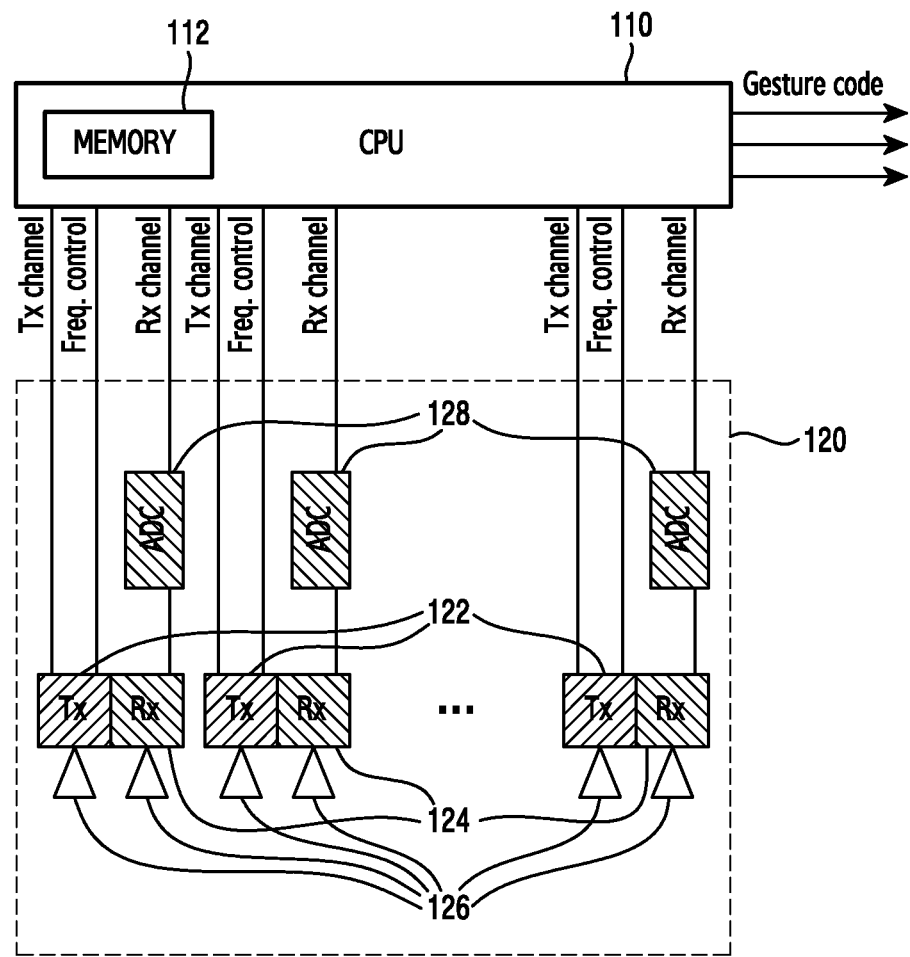
FIG. 3 illustrates, in block diagram format, a device for recognizing a gesture using an RF sensor according to various embodiments of the present disclosure.
Figure 4:
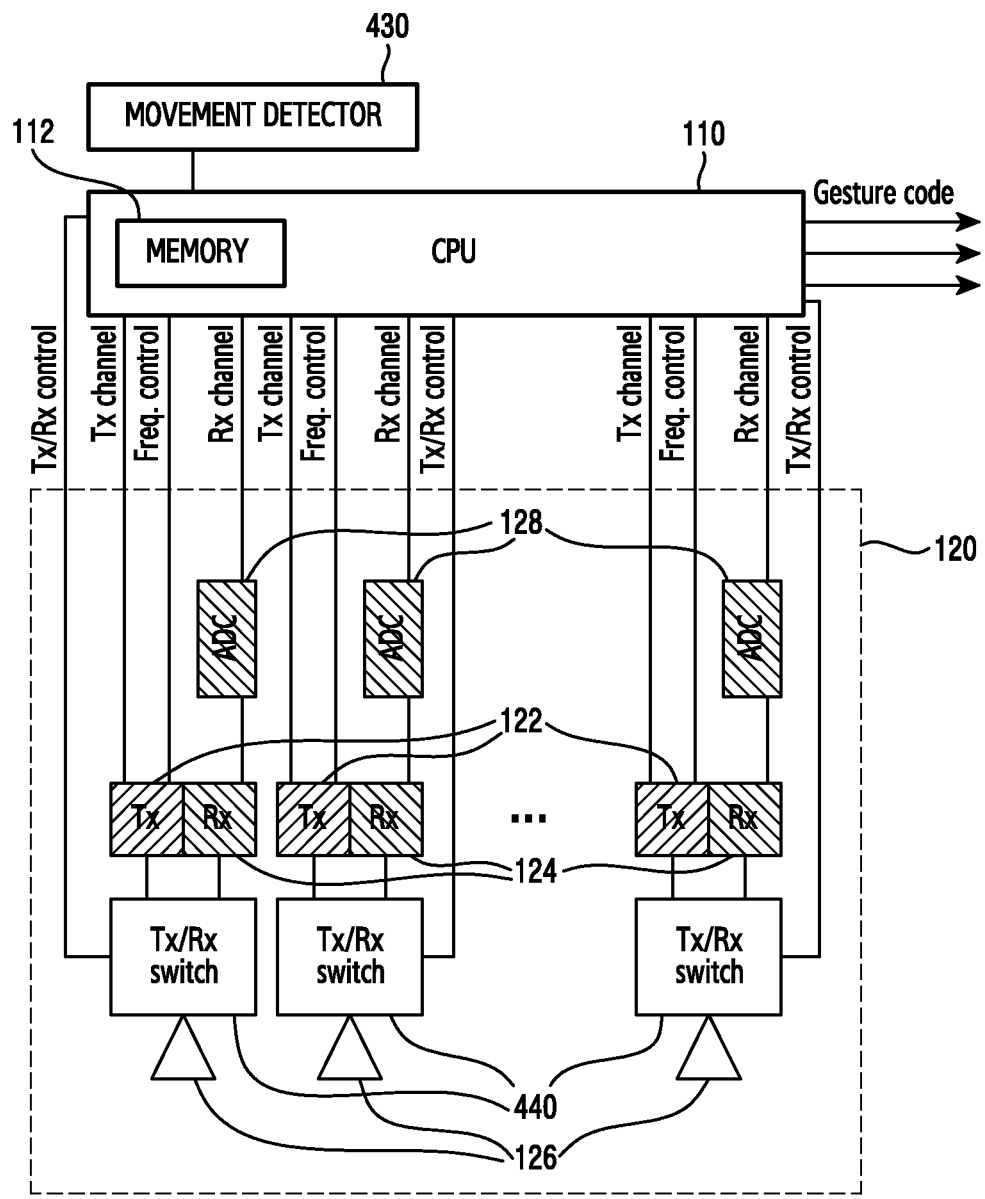
FIG. 4 illustrates, in block diagram format, a device for recognizing a gesture using an RF sensor according to various embodiments of the present disclosure.

FIGS. 3 and 4 illustrate, in block diagram format, a device for recognizing a gesture using an RF sensor according to various embodiments of the present disclosure. A term such as 'part' or '~er' indicates a unit for processing at least one function or operation, and can be implemented using hardware, software, or a combination of hardware and software.

Referring to the non-limiting examples of FIG. 3 and FIG. 4, the gesture recognizing device according to certain embodiments includes a CPU 110 including a memory, and an RF sensor 120 including at least one antenna 126, at least one transmitter (Tx) 122, at least one receiver (Rx) 124, and at least one ADC 128. The numbers of the transmitters 122, the receivers 124, and the ADCs 128 can be one or more respectively. The number of the antennas 126 can correspond to a sum of the number of the transmitters 122 and the number of the receivers 124, or the number of pairs of the transmitters 122 and the receivers 124.

In certain embodiments, the memory 112 is included in the CPU 110. However, the memory 112 can be implemented as a separate unit in the gesture recognizing device. The memory 112 can also include any type of a computer-readable storage device and/or a storage disk. The CPU 110 including the memory 112 can configure a controller. The controller can control operations of the gesture recognizing device.

In some embodiments, antennas 126 are connected to the transmitters 122 and the receivers 124, and transmit and receive RF signals. As shown in FIG. 3, each of the transmitters 122 is connected to one antenna 126, and each of the receivers 124 is connected to other antenna 126. In another embodiment, such as illustrates by FIG. 4, a pair of the transmitter 122 and the receiver 124 is connected to one antenna 126.

In at least one embodiment, in which the pair of the transmitter 122 and the receiver 124 are connected to one antenna 126, the gesture recognizing device can include switches 440. The number of the switches 440 may correspond to the number of the pairs of the transmitters 122 and the receivers 124. Each switch 440 switches the antenna 124 connected thereto. Each switch 440 is controlled by the CPU 110. To emit the RF signals, the switch 440 switches the antenna 126 to the transmitter 122. To receive the RF signals, the switch 440 switches the antenna 126 to the receiver 124.

In some embodiments, transmitter 122 successively generates the RF signals and emits the RF signals into tissues of a user body part via the one antenna 126. The transmitters 122 are configured to operate in a low frequency band of about 1-3 GHz, or according to any other wireless communication standard in the mentioned band. The transmitters 122 are also configured to operate in a high frequency band of about 3-10 GHz, or according to any other wireless communication standard in the mentioned band. Hence, each transmitter 122 emits a set of single RF signals (frequency pulses) in the above-stated low or high frequency band. The transmitters 122 are configured to generate the RF signals having different frequencies in the set. All the RF signals having different frequencies in the set are generated in order to increase the frequency in a stepped manner. In other embodiments, the single RF signals can be generated in a descending order or in any other order. Each of the sets of RF signals is processed as "single measurement" because the sets of RF signals are processed in a shorter time than a typical time of the gesture. In some embodiments, each set of RF signals is emitted periodically, and the period is long enough to process each set in the CPU 110. The CPU 110 controls the transmitters 122 to generate the RF signals within the low frequency band and the high frequency band, and the frequencies of the RF signals are controlled by the CPU 110 via frequency control lines (Freq. control) as shown in FIGS. 3 and 4. The high frequency band applied in the measurements can improve accuracy of the gesture recognition. The frequency band of the generated RF signal sets as an operating frequency band of the transmitters 122 can switch from the low frequency band to the high frequency band while the gesture recognizing device operates. The CPU 110 can, in some embodiments, determine whether a user begins or stops a gesture based on output signals of the ANN. When determining the start of a gesture, the CPU 110 can transmit to the transmitter 122 a command for switching the operating frequency band to the high frequency band to increase a resolution of the gesture recognizing device, so as to improve the accuracy of the gesture recognition. When determining the gesture stopped, the CPU 110 can transmit to the transmitter 122 a command for switching the operating frequency band to the low frequency band so as to save energy of the gesture recognizing device. The operating frequency band can be defined by a manufacturer based on an RF standard, characteristics of human body tissues to provide lowest attenuation of the RF signals, and best resolution for the gesture recognition.

According to certain embodiments, the CPU 110 can control the operating frequency band based on at least one of a battery status of the gesture recognizing device, a running application, and content. For example, when the battery status of the gesture recognizing device falls below a certain level or the application or the content causing considerable battery consumption is running, the gesture recognizing device can switch the operating frequency band to the low frequency band. Also, when the battery status of the gesture recognizing device exceeds a certain level or accurate gesture recognition is required, the gesture recognizing device can switch the operating frequency band to the high frequency band.

The emitted RF signals are, in some embodiments, reflected from the tissues of the user body part. At the same time, the tissues of the user body part distort the RF signals. The distortion of the received RF signal indicates attenuation (amplitude change) and phase shift of the RF signal. The receivers 124 each receives the RF signals reflected from and distorted by the tissues of the user body part. In addition, the receivers 124 separate each received RF signal in each set of the RF signals into a first RF signal and a second RF signal. The first RF signal represents the amplitude and the second RF signal represents the phase shift.

The ADCs 128 are, in certain embodiments, connected to the receivers 124 respectively. The ADCs 128 convert the first RF signals and the second RF signals in each set of the RF signals into digital signals so as to acquire sets of digital signals fed to the CPU 110. Each set of the digital signals is obtained from a corresponding set of the RF signals According to certain embodiments, CPU 110 controls the whole measurement process. The CPU 110 sends a command to generate the sets of the RF signals to the transmitters 122 and reads measurement results as the digital signals from the receivers 124. The CPU 110 implements an ANN stored in the memory 112 of the CPU 110. The CPU 110 is configured to process the sets of the digital signals using the ANN and reference data sets for the gesture recognition. The reference data sets are parameters of the ANN obtained during its learning for the gesture recognition. Each reference data set is associated with a particular gesture and is formed while the ANN learns to recognize the particular gesture. Further, the CPU 110 can determine that the user body part performs a gesture based on an output of the ANN as a non-zero value before the gesture is completely recognized. Such operations of the ANN as learning and testing the ANN are well-known in the related art and accordingly detailed descriptions thereof are not required.

According to other embodiments, the gesture recognizing device can optionally include a movement detector 430 as shown in FIG. 4. In the non-limiting example of FIG. 4, the movement detector 430 can be one of an accelerometer, a magnetic sensor, a barometer, a 3D positioner of the gesture recognizing device which determines its position with respect to a predetermined point (e.g. user head) in space.

Using the gesture recognizing device, the user can perform certain actions such as walking, running, and driving a vehicle. An excessive vibration level of the user's body can affect the accuracy of the gesture recognition. In certain embodiments, such as shown in the non-limiting example of FIG. 4, the movement detector 430 measures the vibration level of the user body part to which the gesture recognizing device is fixed. The measured vibration level is fed to the CPU 110. By use of the ANN, the CPU 110 compares the measured vibration level with a threshold previously obtained by the learning of the ANN and stored in the memory 112. The operating frequency band of the transmitters 122 can change due to a change of the vibration level. When the transmitters 122 generate the sets of the RF signals within the high frequency band and the vibration level exceeds the threshold, the CPU 110 switches the transmitters 122 to generate the RF signals in the low frequency band so as to suppress the excessive vibration influence. When the transmitters 122 generate the sets of the RF signals in the low frequency band and the CPU 110 determines that the user body part conducts a gesture, the generation of the RF signals within the low frequency band continues.

The gesture recognizing device can, depending on embodiments, be a separate device or a device embedded into a wearable device such as a smartwatch, a headphone, and other wearable device, which is to be controlled or controls the device coupled with the wearable device. When the wearable device including the embedded the gesture recognizing device includes a CPU and/or a movement detector, the CPU and/or the movement detector of the wearable device can be used as the CPU 110 and/or the movement detector 430 of the gesture recognizing device.

According to certain embodiments, to obtain the reference data sets associated with particular gestures, the learning of the ANN stored in the memory 112 of the CPU 110 is performed. When the user body part performs a particular gesture, in the ANN learning, the transmitters 122 each generates and emits the set of the RF signals into the tissues of the user body part via the at least one antenna 126. In the non-limiting example of FIG. 4, receivers 124 each receive the set of the RF signals reflected from and distorted by the tissues of the user body part via the antennas 126, and separates each received RF signal into the first RF signal and the second RF signal. The first RF signal represents the amplitude and the second RF signal represents the phase shift. The ADCs 128 each converts the first RF signals and the second RF signals into the digital signals to obtain a set of digital signals. The set of the digital signals is obtained from the set of the RF signals. Using the ANN, the CPU 110 processes the set of the digital signals to obtain the reference data set associated with the gesture, and stores the reference data set in the memory 112. The ANN learning is repeated for each of the gestures, and the reference data set is obtained for each gesture.

According to certain embodiments, to acquire the threshold for the vibration level, the learning of the ANN is carried out. When the user body part conducts the gesture, the vibration level of the user body part is measured by the movement detector 430. The measured vibration level is sent to the CPU 110. The CPU 110 selects a maximum vibration level among the measured vibration levels, assigns the maximum vibration level as the threshold, and stores the threshold in the memory 112.

The gesture recognizing device can, in some embodiments, further include a reflector arranged on a side of the user body part opposite to a side of the user body part into which the RF signals are emitted. The reflector reflects the RF signals emitted into the tissues of the user body part and passing through the user body part, to increase intensity of the reflected RF signal received at the receiver 124. The reflector can be formed of a metal plate. The reflector is attached to a fixing means of the gesture recognizing device, which fixes the gesture recognizing device on the user body part. The fixing means can be any means adapted to fix the gesture recognizing device onto the user body part.

According to some embodiments, the gesture recognizing device can include the RF sensor including the at least one antenna 126, the at least one transmitter 122, the at least one receiver 124, and the at least one DAC, and the controller including the CPU 110. Although not depicted in FIG. 3 and FIG. 4, the gesture recognizing device according to certain embodiments, can further include a communication unit for communicating with other device. The communication unit transmits and receives signals over a radio channel. For example, the communication unit performs a conversion function between a baseband signal and a bit string according to a physical layer standard of a system. Also, the communication unit can include other communication modules for processing signals of different frequency bands. For example, the other communication standards can include Bluetooth Low Energy (BLE), Wireless Fidelity (Wi-Fi), Wi-Fi Gigabyte (WiGig), and a cellular network (e.g., Long Term Evolution (LTE)). The communication unit, which sends and receives signals, can be referred to as a transmitting unit, a receiving unit, or a transceiving unit.

Figure 5:
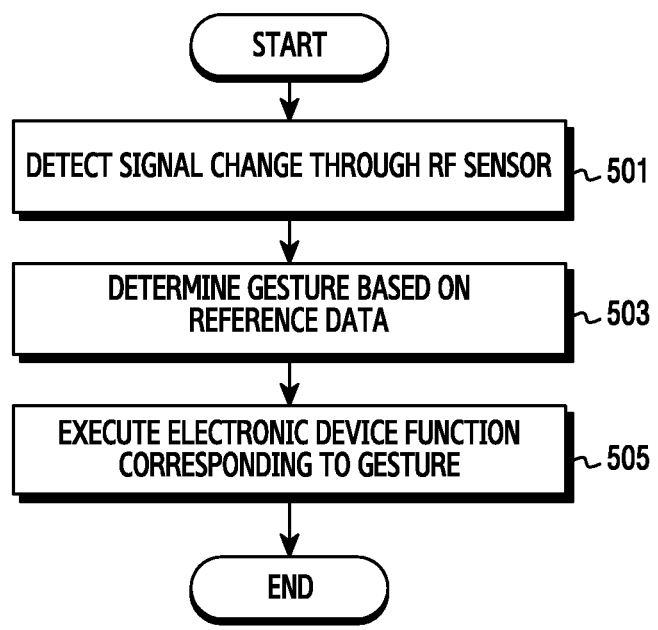
FIG. 5 illustrates, in flowchart format, a method for controlling functions of an electronic device through gesture recognition according to various embodiments of the present disclosure.

FIG. 5 illustrates, in flowchart format, operations of a method for controlling functions of an electronic device through gesture recognition according to various embodiments of the present disclosure. FIG. 5 illustrates the operating method of the gesture recognizing device of FIG. 3 and FIG. 4.

Referring to the non-limiting example of FIG. 5, in operation 501, the gesture recognizing device can detect a change of a signal through the RF sensor. For example, the gesture recognizing device can detect the change of the reflected RF signal waveform by repeatedly emitting an RF signal into a human body and receiving the reflected RF signal. In particular, the gesture recognizing device can detect the change of at least one of the amplitude and the phase of the reflected RF signal. According to an embodiment, the gesture recognizing device can send at least one RF signal to the user body, receive the at least one RF signal reflected from the user body, and then separate the at least one RF signal reflected into a first RF single representing the amplitude and a second RF signal representing the phase. The gesture recognizing device, according to certain embodiments of this disclosure, can convert the first RF signal and the second RF signal to digital signals and thus detect the change of the RF signal when the change exceeds a threshold. That is, when the converted digital signals change over a certain level compared with previous values, the gesture recognizing device can determine a gesture and then determine whether a preset gesture is conducted.

Figure 7:
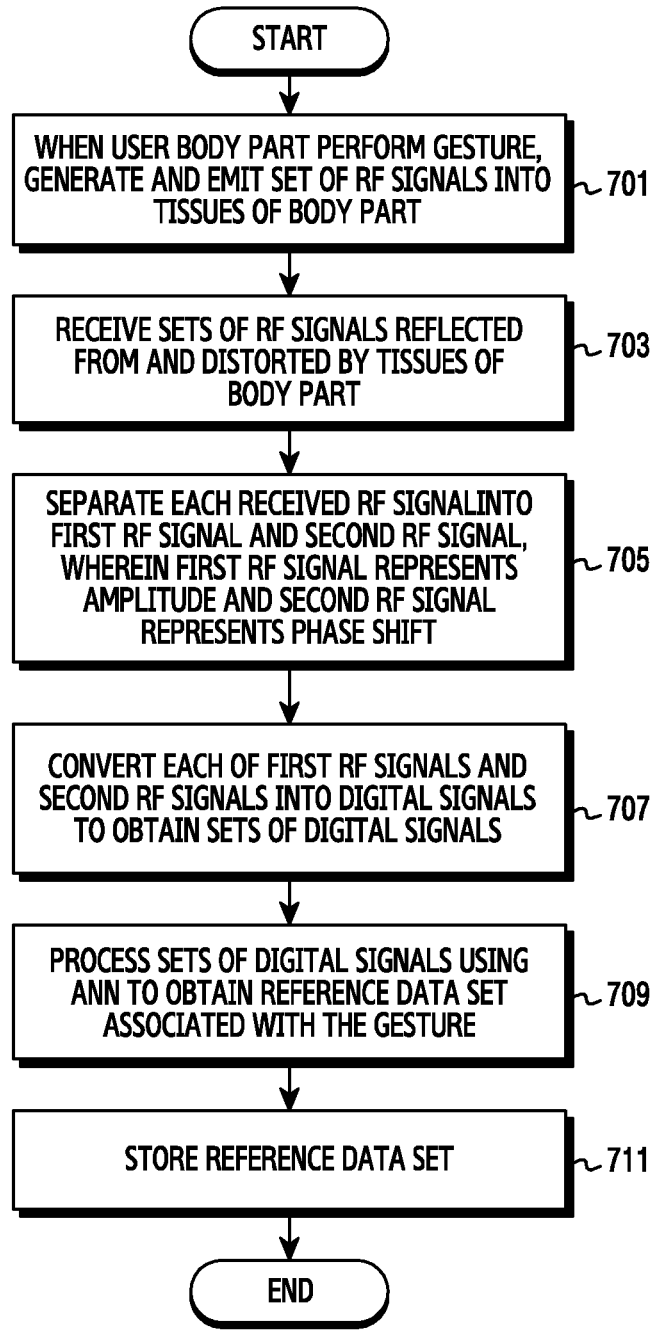
FIG. 7 illustrates, in flowchart format, a learning method of an Artificial Neural Network (ANN) for obtaining a reference data set associated with a gesture according to various embodiments of the present disclosure.
Figure 8:
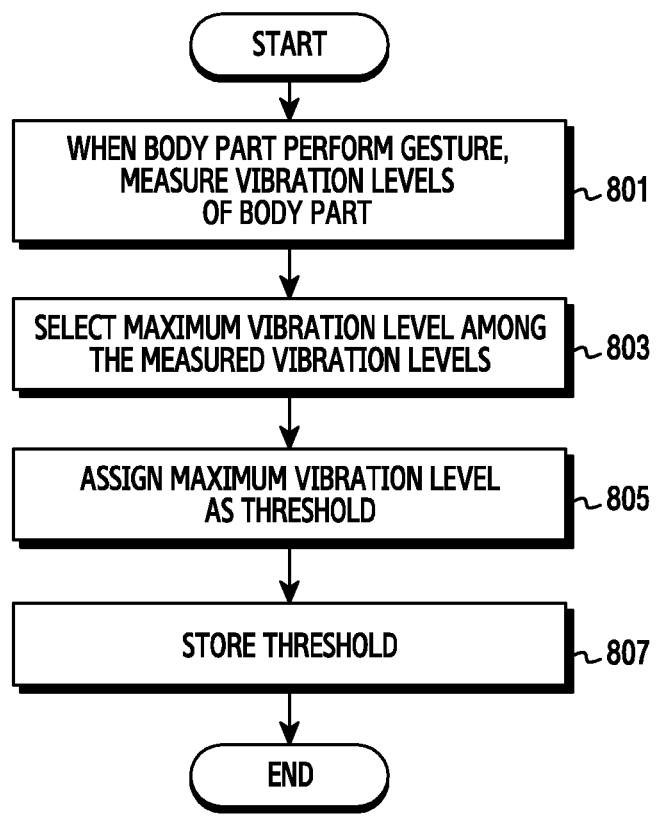
FIG. 8 illustrates, in flowchart format, an ANN learning method for acquiring a threshold for a vibration level according to an embodiment of the present disclosure.

In the non-limiting example of FIG. 5, at operation 503, the gesture recognizing device determines the gesture based on reference data. For example, the gesture recognizing device can determine amplitude attenuation and phase shift of the RF signal by collecting the reflected RF signal waveforms. According to at least one embodiment, when the movement detector 430 determines the vibration level over the threshold, internal vibrations can be determined. Since the vibration level over the threshold can affect the gesture determination, the gesture recognizing device can switch the RF signal generating frequency band to a low frequency band so as to suppress the influence of the excessive vibrations. Next, the gesture recognizing device can go back to operation 501. According to some embodiments, when the movement detector 430 determines the vibration level smaller than threshold, the gesture recognizing device can determine the gesture using the collected RF signals. The gesture recognizing device can determine the gesture by inputting the collecting RF signals to the ANN and comparing with a pre-collected reference data set. According to certain embodiments, the reference data set can be acquired by the gesture recognizing device as shown in FIG. 7, and the threshold for determining the vibration level can be obtained as shown in FIG. 8.

According to some embodiments, at operation 505, the electronic device executes its function corresponding to the gesture. For example, the electronic device can control to execute its predefined function based on the recognized gesture. Herein, according to at least one embodiment, the electronic device can be the same wearable device as the gesture recognizing device. According to another embodiment, the electronic device can be a separate device from the gesture recognizing device, and can receive information about the recognized gesture over wired/wireless communication from the gesture recognizing device and control its function based on the received gesture information.

Figure 6:
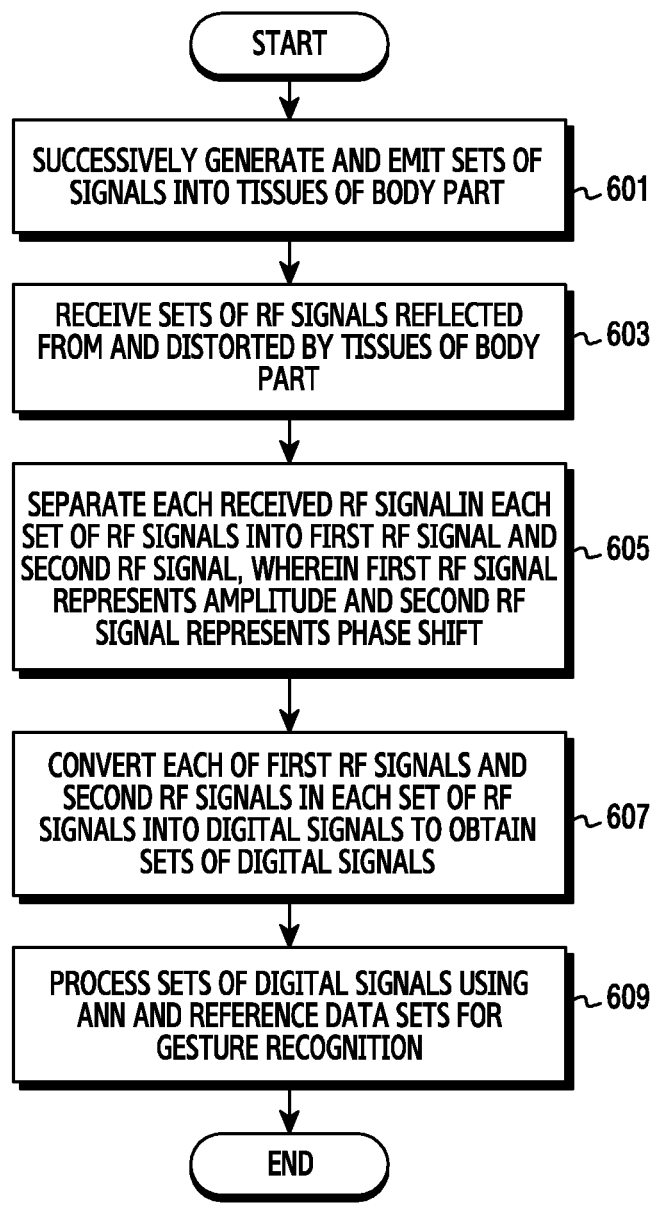
FIG. 6 illustrates, in flowchart format, a method for recognizing a gesture using an RF sensor according to various embodiments of the present disclosure.

FIG. 6 illustrates, in flowchart format, operations of a method for recognizing a gesture using an RF sensor according to various embodiments of the present disclosure. FIG. 6 illustrates certain embodiments of an operating method of the gesture recognizing device of FIG. 3 and FIG. 4. The present method for recognizing gestures using the RF sensor which can be implemented in the gesture recognizing device is now described with reference to the non-limiting examples of FIG. 6 and FIG. 7.

Referring to the non-limiting example of FIG. 6, in operation 601, the at least one transmitter 122 successively generates sets of RF signals and successively emits the sets of the RF signals into tissues of a user body part via at the least one antenna 126. Generating the sets of the RF signals can include generating the RF signals having different frequencies. Generating the sets of the RF signals can include generating the sets of the RF signals in a low frequency band and a high frequency band.

According to certain embodiments, at operation 603, the at least one receiver 124 receives the sets of RF the signals reflected from and distorted by the tissues of the user body part via the at least one antenna 126.

According to certain embodiments, at operation 605, the at least one receiver 124 separates each received RF signal into a first RF signal and a second RF signal. In so doing, the first RF signal represents amplitude and the second RF signal represents phase shift.

According to certain embodiments, at operation 607, the at least one ADC 128 converts each of the first RF signals and the second RF signals in each set of the RF signals into digital signals, in order to obtain sets of digital signals.

According to certain embodiments, at operation 609, the CPU 110 processes the sets of the digital signals using the ANN and reference data sets for gesture recognition. Each reference data set is associated with a particular gesture and obtained by learning of the ANN.

The method according to certain embodiments includes obtaining the digital signals from the sets of the RF signals generated in the low frequency band, processing, at the CPU, the digital signal sets using the ANN and the reference data sets for the gesture recognition, determining that the user's body part conducts the gesture when the ANN outputs a non-zero value before the gesture is completely recognized, and switching at least one transmitter to generate RF signals in the high frequency band.

According to certain embodiments, when the gesture recognizing device further includes the movement detector 430, the method can further include the following operations. In one additional operation, the movement detector 430 measures a vibration level of the user body part. The controller of the gesture recognizing device can control to measure the vibration level of the user body part using the movement detector 430. In another additional operation, the CPU 110 using the ANN compares the vibration level with a threshold. The threshold is obtained through the learning of the ANN. In another additional operation, when the vibration level exceeds the threshold, the CPU 110 switches the at least one transmitter 122 to generate RF signals within the low frequency band when the sets of the RF signals are generated within the high frequency band. In another additional operation, when the vibration level exceeds the threshold, the sets of the RF signals are generated within the low frequency band, and it is determined that the user body part performs a gesture, the CPU 110 controls the at least one transmitter 122 to keep generating the RF signals in the low frequency band.

According to certain embodiments, when the gesture recognizing device includes the one antenna 126 for the pair of the transmitter 122 and the receiver 124, and the switch 440 for switching the antenna 126 between the transmitter 122 and the receiver 124, the method can further include the following operations. In one additional operation, when the RF signal is emitted, the switch 440 switches the antenna 126 to the transmitter 122. In another additional operation, when the RF signal reflected from and distorted by the tissues of the user body part is received, the switch 440 switches the antenna 126 to the receiver 124.

FIG. 7 illustrates, in flowchart format, operations of an ANN learning method for obtaining a reference data set associated with a gesture according to various embodiments of the present disclosure. FIG. 7 illustrates an operating method of the gesture recognizing device of FIG. 3 and FIG. 4. The ANN learning for obtaining the reference data sets associated with gestures is described with reference to the non-limiting example of FIG. 7. The ANN learning is performed for each of gestures and the reference data set is obtained for each gesture.

Referring to the non-limiting example of FIG. 7, in operation 701, when the user body part performs a gesture, the at least one transmitter 122 generates and emits a set of RF signals into the tissues of the user body part via the at least one antenna 126.

According to certain embodiments, at operation 703, the at least one receiver 124 receives the set of the RF signals reflected from and distorted by the tissues of the user body part via the at least one antenna 126.

According to certain embodiments, at operation 705, the at least one receiver 124 separates each received RF signal into a first RF signal and a second RF signal. The first RF signal represents amplitude and the second RF signal represents phase shift.

According to certain embodiments, at operation 707, to obtain a set of digital signals, the at least one ADC converts each of the first RF signals and the second RF signals into digital signals. The set of the digital signals is obtained from the set of the RF signals.

According to certain embodiments, at operation 709, the CPU 110 processes the set of the digital signals by the ANN to obtain a reference data set associated with the gesture. For example, the CPU 110 can obtain a reference data set for a particular gesture by processing the set of the digital signals acquired in operation 707 using the ANN.

According to certain embodiments, at operation 711, the CPU 110 stores the reference data set in the memory. That is, the CPU 110 stores the reference data set acquired in operation 709 in the memory. Next, based on the stored reference data set, the CPU 110 can determine the gesture for the reflected signal pattern.

FIG. 8 illustrates, in flowchart format, operations of an ANN learning method for obtaining a threshold for a vibration level according to some embodiments of the present disclosure. According to some embodiments, FIG. 8 illustrates an operating method of the gesture recognizing device of FIG. 3 and FIG. 4. The ANN learning to acquire the threshold for the vibration level is now explained by referring to FIG. 8.

Referring to the non-limiting example of FIG. 8, when the user body part performs a gesture, the movement detector 430 measures vibration levels of the user body part in operation 801. For example, when detecting a movement of the user body part, the movement detector 430 can measure vibration levels of the user body part. In so doing, the movement detector 430 can include at least one of an accelerometer, a magnetic sensor, a barometer, and a 3D positioner.

According to certain embodiments, at operation 803, the CPU 110 selects a maximum vibration level among the measured vibration levels. That is, the CPU 110 can determine the greatest vibration level from the measured vibration levels.

According to certain embodiments, at operation 805, the CPU 110 assigns the maximum vibration level as the threshold. The CPU 110 can assign the maximum vibration level selected in operation 803, as the threshold for determining to switch the frequency band.

According to certain embodiments, at operation 807, the CPU 110 stores the threshold in the memory. That is, the CPU 110 stores the threshold assigned in operation 805 in the memory. Next, based on the stored threshold, the CPU 110 can determine whether to switch the frequency band to the low frequency band when the vibration level exceeds a certain level.

According to certain embodiments, the learning of ANN for obtaining the reference data sets associated with gestures and the learning of ANN for obtaining the threshold value may be performed separately or as single learning process.

The foregoing descriptions of the embodiments are illustrative, and modifications in configuration and implementation are within the scope of the current description. For instance, while the embodiments are generally described with relation to FIGS. 1-8, those descriptions are exemplary. Although the subject matter has been described in language specific to structural features or methodological acts, it is understood that the subject matter defined in the appended claims is not necessarily limited to the specific features or acts described above. Rather, the specific features and acts described above are disclosed as example forms of implementing the claims. Embodiments are not limited by the illustrated order of the method steps, the order may be modified by a skilled person without creative efforts. Some or all of the method steps may be performed sequentially or concurrently.

The method and the electronic device according to various embodiments of the present disclosure can determine the user's gesture using the RF sensor, control the function of the electronic device according to the gesture, and thus provide the function control method of the electronic device more quickly and easily. Additionally, the electronic device according to certain embodiments of this disclosure can achieve continuous monitoring (gesture processing while the user is moving), can be embedded into various wearable devices (e.g., a watch, a headphone, etc.), does not need direct (electrical) contact to skin, and can determine the gesture through clothes (e.g., gloves, costume, shirt, trousers, etc.). Further, embodiments of the gesture recognizing device and the methods for operating same according to this disclosure need not be tightly affixed on the user's body by means of the RF signals having wavelengths greater than possible distances of displacement on the user's body part. Additionally, embodiments according to this disclosure may be able to ignore movements of other user's body parts not related to the user's body part (e.g., hands, neck, etc.) of which movements are detected. Additionally, embodiments according to this disclosure can use only one user's body part in the device control, can easily control the device by gesture, do not need to place active components (e.g., sensors, antennas) inside a strap, may require a small number of sensors (antennas), and may provide low power consumption and harmlessness for the user because a power of the emitted signals is low in view of the RF signals and the RF signals have low attenuation inside the body, bones, and so on.

The methods according to the embodiments described in the claims or the specification of the present disclosure can be implemented in software, hardware, or a combination of hardware and software.

As for the software, according to certain embodiments, a computer-readable storage medium storing one or more programs (software modules) can be provided. One or more programs stored in the computer-readable storage medium can be configured for execution by one or more processors of the electronic device. One or more programs can include instructions for controlling the electronic device to execute the methods according to the embodiments described in the claims or the specification of the present disclosure.

Such a program (software module, software) can be stored to a random access memory, a non-volatile memory including a flash memory, a Read Only Memory (ROM), an Electrically Erasable Programmable ROM (EEPROM), a magnetic disc storage device, a Compact Disc (CD)-ROM, Digital Versatile Discs (DVDs) or other optical storage devices, and a magnetic cassette. Alternatively, the program can be stored to a memory combining part or all of those recording media. A plurality of memories may be equipped.

In some embodiments, program can be stored in an attachable storage device accessible via a communication network such as Internet, Intranet, Local Area Network (LAN), Wide LAN (WLAN), or Storage Area Network (SAN), or a communication network by combining these networks. The storage device can access the electronic device through an external port. A separate storage device may access the present device over the communication network.

The elements identified in the disclosure as components or operations of embodiments according to this disclosure are expressed in a singular or plural form. However, the singular or plural expression is appropriately selected according to a proposed situation for the convenience of explanation and the present disclosure is not limited to a single element or a plurality of elements. The elements expressed in the plural form may be configured as a single element, and the elements expressed in the singular form may be configured as a plurality of elements.

While this disclosure has been described with reference to certain exemplary embodiments thereof, it will be understood by those skilled in the art that various changes in form and details may be made therein without departing from the spirit and scope of the present disclosure.

Although the present disclosure has been described with various embodiments, various changes and modifications may be suggested to one skilled in the art. It is intended that the present disclosure encompass such changes and modifications as fall within the scope of the appended claims.

What is claimed is:

1. A method performed by an electronic device, the method comprising:
    measuring a vibration level of a body using at least one sensor;
    determining whether the measured vibration level exceeds a preset threshold;
    generating a radio frequency (RF) signal within a low frequency band in case that the vibration level exceeds the preset threshold;
    emitting the RF signal into the body;
    receiving a reflected RF signal that is changed based on a reflection of the emitted RF signal from the body;
    identifying a gesture of the body based on the reflected RF signal and reference data for at least one gesture; and
    executing a function of the electronic device corresponding to the identified gesture.

2. The method of claim 1, further comprising:
    determining the reference data based on the reflected RF signal.

3. The method of claim 2, wherein the determining the reference data comprises:
    emitting the RF signal to the body while a user of the electronic device conducts a particular gesture;
    receiving the reflected RF signal from the body; and
    determining the reference data for the particular gesture based on the reflected RF signal.

4. The method of claim 3, wherein the determining the reference data for the particular gesture based on the reflected RF signal comprises:
    separating the reflected RF signal into a first RF signal representing amplitude and a second RF signal representing phase;
    converting the first RF signal and the second RF signal to digital signals; and
    determining the reference data for the particular gesture by processing the digital signals based on artificial neural network (ANN) learning.

5. The method of claim 1, wherein the identifying a gesture of the body comprises:
    identifying a change of the RF signal based on comparison of the reflected RF signal and the emitted RF signal.

6. The method of claim 5, wherein the identifying the gesture of the body comprises:
    separating the reflected RF signal into a first RF signal representing amplitude and a second RF signal representing phase;
    converting the first RF signal and the second RF signal to digital signals; and determining the gesture by processing the digital signals based on ANN learning.

7. The method of claim 1, further comprising:
if a user of the electronic device conducts a gesture, measuring vibration levels of the body;
selecting a maximum vibration level from the measured vibration levels; and
determining the maximum vibration level as the preset threshold.

8. The method of claim 1, further comprising:
if the measured vibration level exceeds the preset threshold and an operating frequency band is a high frequency band, switching the operating frequency band to a low frequency band.

9. The method of claim 1, further comprising:
if the measured vibration level falls below the preset threshold, maintaining an operating frequency.

10. An electronic device comprising:
a radio frequency (RF) sensor; and
at least one processor functionally coupled with the RF sensor,
wherein the at least one processor is configured to:
measure a vibration level of a body using at least one sensor;
determine whether the measured vibration level exceeds a preset threshold;
generate an RF signal within a low frequency band in case that the vibration level exceeds the preset threshold;
emit the RF signal into a body;
receive a reflected RF signal that is changed based on a reflection of the emitted RF signal from the body;
identify a gesture of the body based on the reflected RF signal and reference data for at least one gesture; and
execute a function of the electronic device corresponding to the identified gesture.

11. The electronic device of claim 10, wherein the at least one processor is configured to determine the reference data based on the reflected RF signal.

12. The electronic device of claim 11, wherein the RF sensor is configured to emit the RF signal to the body while a user of the electronic device conducts a particular gesture, and to receive the reflected RF signal reflected from the body, and
wherein the at least one processor is further configured to determine the reference data for the particular gesture based on the reflected RF signal.

13. The electronic device of claim 12, wherein the at least one processor is further configured to:
separate the reflected RF signal into a first RF signal representing amplitude and a second RF signal representing phase,
convert the first RF signal and the second RF signal to digital signals, and
determine the reference data for the particular gesture by processing the digital signals based on artificial neural network (ANN) learning.

14. The electronic device of claim 10, wherein the RF sensor is configured to:
identify a change of the RF signal based on comparison of the reflected RF signal and the emitted RF signal.

15. The electronic device of claim 14, wherein the at least one processor is further configured to:
separate the reflected RF signal into a first RF signal representing amplitude and a second RF signal representing phase,
convert the first RF signal and the second RF signal to digital signals, and
determine the gesture by processing the digital signals based on ANN learning.

16. The electronic device of claim 10, wherein the at least one processor is further configured to:
measure vibration levels of the body if a user of the electronic device conducts a gesture,
select a maximum vibration level from the measured vibration levels, and
determine the maximum vibration level as the preset threshold.

17. The electronic device of claim 10, wherein, if the measured vibration level exceeds the preset threshold and an operating frequency of the RF sensor is a high frequency band, the at least one processor is further configured to switch an operating frequency band of the RF sensor to a low frequency band.

18. The electronic device of claim 10, wherein, if the measured vibration level falls below the preset threshold, the at least one processor is further configured to maintain an operating frequency of the RF sensor.

19. The method of claim 4, further comprising:
if the ANN outputs a non-zero value before the gesture is recognized, switching an operating frequency band from the low frequency band to a high frequency band.

20. The electronic device of claim 13, wherein the at least one processor is further configured to:
if the ANN outputs a non-zero value before the gesture is recognized, switch an operating frequency band from the low frequency band to a high frequency band.

* * * * *